United States Patent [19]

Whited

[11] Patent Number: 4,538,606

[45] Date of Patent: Sep. 3, 1985

[54] ENDOTRACHEAL TUBE

[76] Inventor: Robert E. Whited, 7157 Hamilton Hills Dr., Cincinnati, Ohio 45244

[21] Appl. No.: 448,632

[22] Filed: Dec. 10, 1982

[51] Int. Cl.³ .............................................. A61M 25/00
[52] U.S. Cl. ................................. 128/207.15; 604/101
[58] Field of Search ...................... 128/207.14, 207.15; 604/96, 101

[56] References Cited

U.S. PATENT DOCUMENTS

| 3,915,173 | 10/1975 | Brekke . | |
|---|---|---|---|
| 4,090,518 | 5/1978 | Elam . | |
| 4,091,816 | 5/1978 | Elam | 128/207.15 |
| 4,230,108 | 10/1980 | Young . | |
| 4,233,984 | 11/1980 | Walling . | |
| 4,235,239 | 11/1980 | Elam | 128/207.15 |
| 4,327,720 | 5/1982 | Bronson et al. . | |
| 4,341,210 | 7/1982 | Elam | 128/207.15 |
| 4,423,725 | 1/1984 | Baran et al. | 128/207.15 |

Primary Examiner—C. Fred Rosenbaum
Assistant Examiner—Michelle N. Lester
Attorney, Agent, or Firm—Wood, Herron & Evans

[57] ABSTRACT

An endotracheal device comprises an air tube adapted to be inserted through the oral or nasal passage and into the trachea to provide an air passage for respirating a patient. The air tube includes an inflatable cuff mounted at the distal end, and a membrane containing a cushioning material disposed along the air tube adjacent the cuff in a position to prevent direct contact between the air tube and the cricoarytenoid joint and its surrounding tissues.

11 Claims, 3 Drawing Figures

ENDOTRACHEAL TUBE

FIELD OF THE INVENTION

This invention relates generally to the area of endotracheal tubes, and, more particularly, to an improved endotracheal tube capable of reducing the incidence and severity of cricoarytenoid trauma.

BACKGROUND OF THE INVENTION

Endotracheal tubes have been routinely used for a number of decades to prevent upper airway obstruction or to facilitate artificial ventilation of unconscious or anesthetized patients. Early designs of endotracheal tubes consisted of a relatively pliable tube shaped for insertion through the oral passage and into the trachea, and adapted to connect to a respirator for the introduction of air into the lungs. To avoid the escape of air from the trachea out the oral and nasal passages, improved endotracheal tubes were later introduced which included an inflatable bag-like structure or cuff disposed about the exterior surface of the tube at the distal end. These newer endotracheal tubes, which are in common use today, are inserted into the trachea such that the cuff is disposed a few centimeters below the larynx. Once in place, the cuff is inflated by a source of air and creates an airtight seal between the tube and tracheal wall. This effectively prevents air being pumped by a respirator into the lungs from escaping the trachea and entering the oral and nasal passages.

Further research resulted in the development of two-cuff endotracheal tubes which generally consist of an esophageal cuff and an oral cuff. Properly positioned in a patient, the two-cuff endotracheal tubes are operable to seal the esophagus and prevent the contents of the stomach from entering the lungs, while also preventing the escape of air being pumped into the lungs from the trachea.

These improvements of endotracheal tubes have encouraged physicians to prescribe prolonged endotracheal intubation of from several days to two or more weeks for some patients. However, particularly over longer intubation periods, several problems have been identified in the use of existing endotracheal tube designs. It was discovered that in an effort to create a non-leak seal between the cuff and walls of the trachea that the pressure applied by the cuff had a tendency to damage the ciliated endothelium of the trachea and occlude the blood perfusion of the tracheal mucosa after a period of time leading to tissue necrosis. In addition, it was found that some patients experienced laryngeal dysfunction due to contact of the endotracheal tube within the posterior endolarynx.

Initial studies of the problems encountered in the use of known endotracheal tubes resulted in attempts at improved designs such as disclosed in U.S. Pat. No. 4,091,816 to Elam. The Elam patent discloses an endotracheal tube with a double cuff arrangement wherein a standard cuff is mounted on the exterior surface of the tube adjacent its distal end, and a second cuff is disposed upwardly along the tube from the lower cuff. The two cuffs are interconnected so that air pumped into one cuff may be transferred to the other. With the endotracheal tube of Elam properly positioned in a patient, the lower cuff is disposed a few centimeters below the larynx within the mid-trachea and the upper cuff a few centimeters above the larynx.

The interconnection between the two cuffs in the Elam patent is intended to solve the problem created by overpressurizing the single cuffs found in prior art endotracheal tubes to avoid damage to the ciliated endothelium of the trachea and possible tissue necrosis. The volume of air in the lower cuff which seals the trachea is transferable to the upper cuff to avoid undue pressure on the tracheal walls while maintaining an airtight seal between the tube and tracheal walls.

In addition, the Elam patent suggests that laryngeal dysfunction is brought about by contact of the endotracheal tube with the vocal cords of the larynx, particularly as a result of the to-and-fro motion of the tube induced by the operation of the respirator as it provides air to the lungs. To reduce the abrasion to the vocal cords caused by such tube motion, the two cuffs along the Elam endotracheal tube are deliberately placed on either side of the larynx. This arrangement is intended to anchor the tube in relation to the larynx so as to prevent or at least limit the to-and-fro movement of the tube against the vocal cords.

Careful study of the effects of prolonged endotracheal intubation has provided a much more accurate appreciation of the true cause of laryngeal injury than suggested in the prior art. It is clear that laryngeal dysfunction is brought about by mechanical trauma of the endotracheal tube as it rides within the posterior endolarynx. This mechanical trauma is imposed by constant and ongoing forces applied by the tube which are related to respirator-induced tube movement, patient movement and reflex laryngeal movement against the tube.

Importantly, it has been discovered that such mechanical trauma is directed to a large extent against the arytenoids and in particular the cricoarytenoid joint and surrounding tissue where the endotracheal tube actually rests when properly positioned in a patient. As an inherent result of the shape of existing endotracheal tubes, the cricoarytenoid joint region becomes a fulcrum or pivot point about which the tube pivots and moves in response to forces applied to the tube by operation of a respirator or by movement of the patient's head and neck.

It has been observed and determined that the resultant effect of such mechanical trauma is potentially serious laryngeal dysfunction. One specific form of laryngeal dysfunction observed is the initiation of traumatic cricoarytenoid arthritis. While generally not permanent, even transient laryngeal dysfunction resulting from cricoarytenoid arthritis may be serious to some patients. As has been documented, the development of cricoarytenoid arthritis may result in a loss or impairment of the laryngeal sphincteric function wherein the cricoarytenoid joint fails to fully close the tracheal tube during swallowing or open during respiration. Without proper sphincteric function to fully seal the trachea, aspiration may occur with the accompanying adverse pulmonary effects. Aspiration is always dangerous, but it can be catastrophic for an already accutely or chronically ill patient with minimal reserves. Failure of the cricoarytenoid joint to fully open may result in a compromised airway into the trachea where the vocal cords do not move open because of the injury to the joint and surrounding tissue. In some cases, injury to the cricoarytenoid joint and surrounding tissue may result in permanent scarring. Any scarring at this site is extraordinarily difficult to correct surgically and may necessitate a permanent tracheotomy.

It is therefore an object of this invention to provide an improved endotracheal tube which eliminates or at least reduces laryngeal dysfunction.

It is another object of this invention to provide an improved endotracheal tube capable of cushioning and protecting the cricoarytenoid joint region including the vocal process and body of the arytenoids, the interarytenoid spae and the intraluminar surface of the cricoid in its porterior one-half, to assure proper laryngeal sphincteric function upon extubation of the tube.

It is a further object of this invention to provide an improved tracheal tube having the dual capability of sealing the trachea without damage to the tracheal walls while protecting the cricoarytenoid joint region from trauma.

SUMMARY OF THE INVENTION

These and other objects are accomplished in this invention of an endotracheal device comprising an elongated pliable air tube shaped for insertion through the oral or nasal passage and into the trachea to provide a passage for pumping air into the lungs. The distal end of the tube is provided with a bag-like membrane or cuff which is adapted to be inflated once the tube is positioned in the trachea so as to create a seal between the tube and trachea without exerting traumatizing forces against the tracheal mucosa or ciliated endothelium of the trachea.

The endotracheal device further includes a second cuff or membrane mounted on the exterior surface of the air tube in a position to contact and cushion the cricoarytenoid joint when the tube is placed in the proper position within the trachea. The cushioning membrane may be filled with air either before or after insertion of the tube or may contain a resilient substance such as silicon or a suitable equivalent. The membrane is spaced from the lower cuff at the distal end of the tube and may extend only partially about the exterior circumference of the tube. The membrane contacts the cricoarytenoid joint thus urging the endotracheal tube upwardly out of direct contact therewith, and adjacent or into engagement with the vocal cords of the larynx. Mechanical trauma to the cricoarytenoid joint caused by motion of the tube within the posterial endolarynx is thus effectively avoided to eliminate or at least substantially reduce cricoarytenoid injury.

DESCRIPTION OF THE DRAWINGS

The structure, operation and advantages of this invention will become apparent upon consideration of the following discussion taken in conjunction with the accompanying drawings wherein.

DETAILED DESCRIPTION OF THE INVENTION

Figure 1:
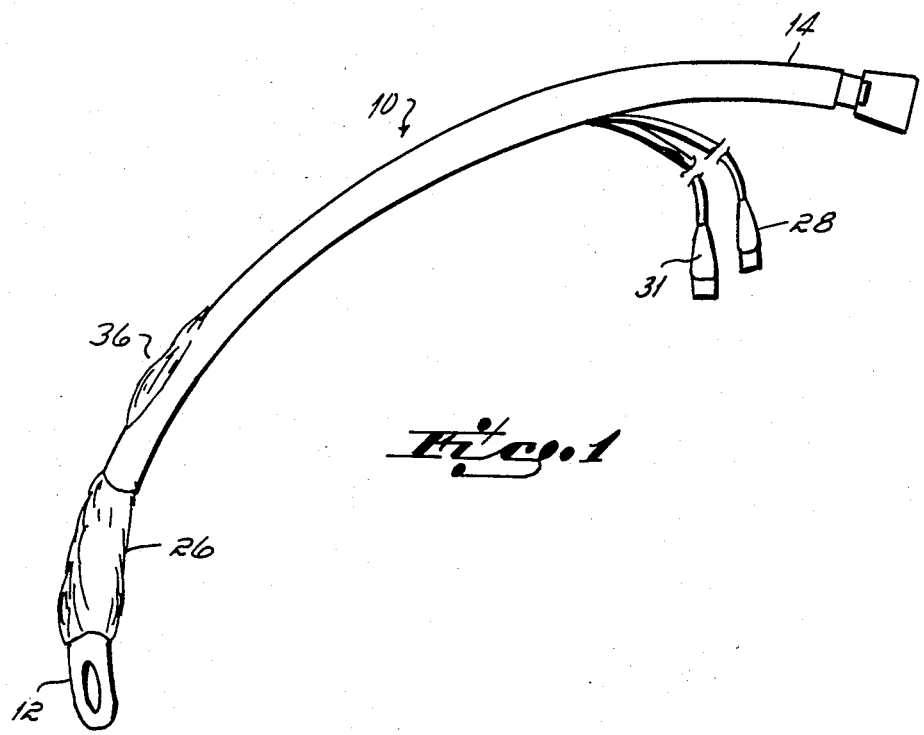
FIG. 1 is a perspective view of the improved endotracheal tube herein.
Figure 3:
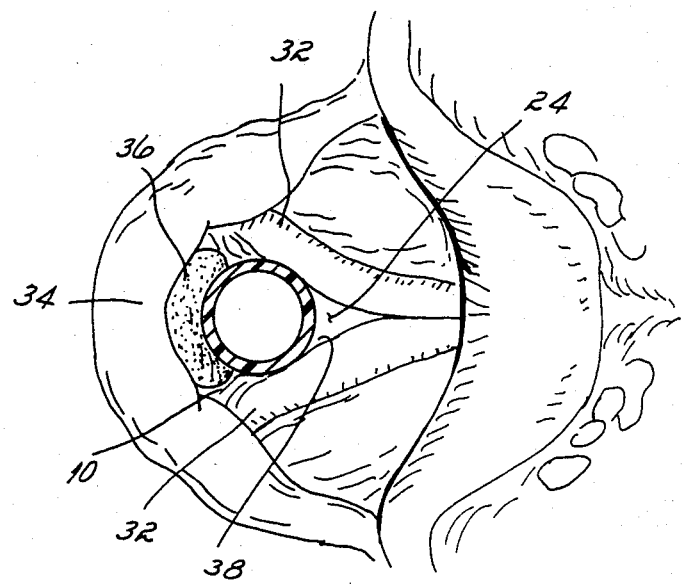
FIG. 3 is a cross-sectional view taken generally along line 3—3 of FIG. 2.

Referring now to FIG. 1, the endotracheal device according to this invention includes an air tube 10 having a distal end 12 and a proximal end 14 adapted for connection to a respirator (not shown). The tube 10 is shaped for insertion through the oral passage 16, past the epiglottis 18 and posterior pharyngeal wall 20, and then through the larynx 22 so that the distal end 12 of the tube 10 enters several centimeters into the trachea 24. Adjacent the distal end 12 of the tube 10 is a bag-like membrane or cuff 26 which is mounted to the exterior surface of the tube 10 and extends outwardly therefrom. The cuff 26 is inflatable by means of a tube 28 connected to a source of air (not shown). With the tracheal tube 10 in proper position in a patient, the cuff 26 extends beyond the larynx 22 and into the trachea 24. Conventionally, the cuff 26 is inflated with sufficient pressure so as to create a seal between the distal end 12 of the tube 10 which prevents the escape of air upwardly through the trachea 24 and out the oral passage 16. Preferably, the pressure used to inflate the cuff 26 is monitored to create a good seal without exerting undue pressure on the walls of the trachea 24 which can lead to damage as discussed above. The structure and materials used in the fabrication of the endotracheal device discussed thus far is typical of that found in many conventional endotracheal tubes for artificial ventilation of unconscious or anesthesized patients or to prevent upper airway obstruction.

Figure 2:
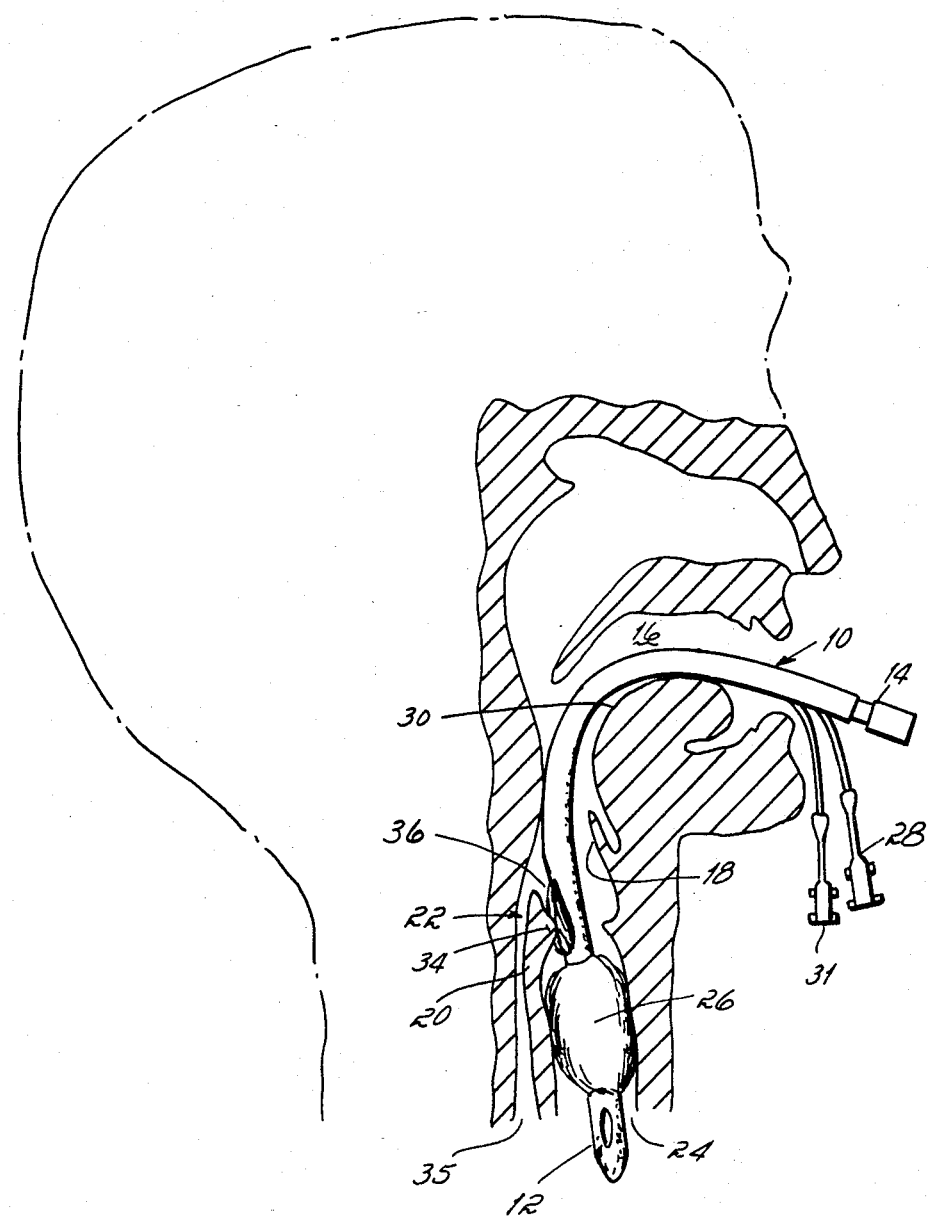
FIG. 2 is a partial cross-sectional, partial schematic view of the endotracheal tube herein installed in a patient.

It has been found that an important limitation of prior art endotracheal tubes, such as the endotracheal device thus far described, is the creation of laryngeal dysfunction in some patients. As illustrated in FIG. 2, the air tube 10 is shaped such that it contacts the tongue 30 near its proximal end 14 and the area of the larynx 22 adjacent its distal end 12. Specifically, it has been found that typical endotracheal tubes directly contact the arytenoids 32, the cricoarytenoid joint 34 and surrounding tissue. The cricoarytenoid joint 34 operates to sphincter or close together the arytenoids 32 during swallowing so that solid or liquid material passes into the esophagus 35 and not the trachea 24. To avoid aspiration and the accompanying pulmonary effects, such as pneumonia, the cricoarytenoid joint 34 must function to seal the trachea 24 fluid tight. In addition, during respiration the cricoarytenoid joint 34 must fully open to provide an unrestricted airway for passage of air in the trachea 24 and lungs.

As mentioned above, endotracheal tubes inherently impose a degree of mechanical trauma within the posterial endolarynx. This trauma is caused by to and fro movement of the tube in response to the operation of the respirator, and also tube movement induced by reflex and laryngeal movements against the tube resulting from swallowing and movement of the head and neck. Considering the positioning of the tube in the posterial endolarynx as shown in FIG. 1 and discussed above, it was discovered that the cricoarytenoid joint 34 and surrounding tissue namely the vocal process and body of the arytenoids, the interarytenoid space and the intraluminar surface of the cricoid in its posterior one-half, in effect functions as a pivot point or fulcrum on which the tube pivots as a result of such laryngeal and tube movements. As a result, of this relatively severe stress placed on the sensitive cricoarytenoid joint 34, laryngeal dysfunction in the form of traumatic cricoarytenoid arthritis and permanent scarring of the cricoarytenoid joint region can be developed in an unacceptable number of patients.

In view of the cause of such laryngeal dysfunction, the endotracheal tube 10 of this invention includes a second cuff or membrane 36 mounted on the exterior surface of the tube 10. The second cuff or membrane 36 may be formed of the same material as the standard cuff 26, and is mounted to tube 10 by an adhesive or any other suitable means. Membrane 36 is disposed adjacent to the cuff 26 at a point along the endotracheal tube 10 which is coincident with the cricoarytenoid joint 34 when the tube 10 is properly placed within the trachea 24. The membrane 36 rests directly on the cricoarytenoid joint 34 thus disposing the endotracheal tube 10 outwardly out of contact therewith and adjacent to or in engagement with the vocal cords 38 of the larynx 22.

The membrane 36 is attached to the exterior surface of endotracheal tube 10 along at least a portion of the circumference thereof. Membrane 36 may be inflated with air after insertion of the tube 10 within the trachea 24, as is cuff 26, or may be preinflated by means of a tube 31 connected to a source of air (not shown). Alternately, the membrane 36 may be filled with a resilient, cushioning material such as a sponge or silicon rubber. It is contemplated that membrane 36 may be spaced from or adjacent to cuff 26 along tube 10, provided that it completely protects the cricoarytenoid joint 34 from engagement with tube 10. The membrane 36 is resilient and provides a cushioning effect to reduce transmittal of traumatic forces to the cricoarytenoid joint 34 caused by motion of the endotracheal tube 10. As shown in FIGS. 1 and 2, the membrane 36 is relatively small in size and thus would not impair the attendant's vision during insertion of the endotracheal tube 10 or interfere with extubation of the tube 10.

It is believed that the addition of membrane 36 to the endotracheal tube 10 of this invention will greatly reduce the chances of aspiration, permanent scarring or other serious laryngeal dysfunction. Although it is possible that contact of the tube 10 with the vocal cords 38 may increase trauma or abrasion of the vocal cords 38, it is believed that the vocal cords 38 are much better able to withstand such trauma than the cricoarytenoid joint 34 and surrounding tissue. Obviously, transient abrasion to the vocal cords 38 is much more preferable than trauma induced arthritis to the cricoarytenoid joint 34 in view of the relative seriousness of the damage which can result from a failure of the sphinteric function of the cricoarytenoid joint 34.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An endotracheal tube adapted for insertion through the oral or nasal passage of a patient to provide a passage for artificial respiration comprising:
    an elongated, flexible air tube having a proximal end portion adapted to be located external to the patient and a distal end portion adapted to be located within the trachea;
    means for sealing the air tube with respect to the trachea, said sealing means being capable of sealing the trachea at a point spaced from the subglottis; and
    cushioning means covering at least a portion of the external wall surface of said air tube and being located such that on insertion of said tube in said patient said cushioning means lies between the cricoarytenoid joint and said external wall surface of said air tube to prevent contact of said air tube with the cricoarytenoid joint to reduce the incidence and severity of cricoarytenoid trauma.

2. The endotracheal device of claim 1 wherein said cushioning means is an air-inflatable membrane attached at least part way about the outer surface of said air tube along a portion of the length thereof.

3. The endotracheal device of claim 1 wherein said cushioning means is a membrane pre-inflated with air and attached at least part way about the outer surface of said air tube along a portion of the length thereof.

4. The endotracheal device of claim 1 wherein said cushioning means is a membrane containing pliable, resilient material.

5. The endotracheal device of claim 1 wherein said sealing means is an inflatable cuff mounted to the distal end of said air tube inserted within the trachea, said cushioning means being spaced from said cuff in the direction of said proximal end of said tube.

6. An endotracheal device for respirating a patient comprising:
    a flexible air tube having a proximal end, distal end and outer surface, said air tube being adapted for insertion through the oral or nasal passage and into the trachea of the patient with said distal end being disposed within said trachea, said air tube providing a passage for respiration of the patient;
    a first air-inflatable cuff adjacent said distal end of said tube, said cuff being inflatable to create a seal between said air tube and said trachea when inserted in the patient, said cuff being capable of sealing the trachea at a point spaced from the subglottis; and
    a second cuff covering at least a portion of said outer surface of said air tube, said second cuff being positioned along said air tube such that on insertion of said tube in said patient said second cuff lies between the cricoarytenoid joint and said outer surface of said air tube to prevent contact of said air tube with the cricoarytenoid joint to reduce the incidence and severity of cricoanytenoid trauma.

7. The endotracheal device of claim 6 wherein said second cuff is a membrane sealed to a portion of the outer surface of said tube and containing a flexible, cushioning material.

8. The endotracheal device of claim 7 wherein said second cuff is inflated with air.

9. The endotracheal device of claim 7 wherein said second cuff contains a liquid.

10. The endotracheal device of claim 6 wherein said second cuff is an air-inflatable membrane attached at least part way about said outer surface of said air tube along at least a portion of the length thereof.

11. The endotracheal device of claim 6 wherein said second cuff is a membrane pre-inflated with air and attached at least part way about the outer surface of said air tube along at least a portion of the length thereof.

* * * * *